United States Patent [19]
Devos et al.

[11] Patent Number: 5,455,337
[45] Date of Patent: Oct. 3, 1995

[54] DNA ENCODING CHIMERIC POLYPEPTIDES COMPRISING THE INTERLEUKIN-5 RECEPTOR α-CHAIN FUSED TO IMMUNOGLOBULIN HEAVY CHAIN CONSTANT REGIONS

[75] Inventors: Rene Devos, Oostende; Walter Fiers, Destelbergen; Jose van der Heyden, Munte; Geert Plaetinck, Destelbergen; Jan Tavernier, Balegem, all of Belgium

[73] Assignee: Hoffmann-La Roche Inc., Nutley, N.J.

[21] Appl. No.: 947,130

[22] Filed: Sep. 16, 1992

[30] Foreign Application Priority Data

Sep. 18, 1991 [EP] European Pat. Off. ............ 91810738

[51] Int. Cl.$^6$ ............................ C07H 21/04; C12N 1/21; C12N 5/10; C12N 15/11
[52] U.S. Cl. .................. 536/23.4; 536/23.5; 536/23.53; 435/69.1; 435/69.7; 435/70.2; 435/240.2; 435/252.3; 435/320.1
[58] Field of Search .................. 536/23.4, 23.5, 536/23.53; 435/69.1, 69.7, 70.2, 240.2, 252.3, 320.1

[56] References Cited

FOREIGN PATENT DOCUMENTS

| | | |
|---|---|---|
| 325262 | 7/1989 | European Pat. Off. . |
| 0890308 | 10/1989 | European Pat. Off. . |
| 394827 | 4/1990 | European Pat. Off. . |
| 417563 | 8/1990 | European Pat. Off. . |
| 464533 | 6/1991 | European Pat. Off. . |
| 475746 | 9/1991 | European Pat. Off. . |
| 91/08298 | 6/1991 | WIPO . |

OTHER PUBLICATIONS

Murata et al *J. Exp. Med* 175, 1992, pp. 341–351.
Groos et al, *PNAS* 86, 1989, pp. 10024–10028.
Aruffo and Seed, Proc. Natl. Acad. Sci. USA 84, 8573 (1987).
Birnboim and Doly, Nucl. Acids. Res. 7, 1513 (1979).
Clutterbuck et al., Eur. J. Immunol. 17, 1743–1750 (1987).
Cullen, Cell, 46, 973–982 (1986).
Felgner et al., Proc. Natl, Acad. Sci. USA 84, 7413–7417 (1987).
German, C., "DNA Cloning" (vol. II., edt. by Glover, D. M., IRL Press, Oxford, 1985).
Huck et al., Nucl. Acids Res. 14, 1779–1789 (1986).
Lopez et al., J. Exp. Med. 167, 219–224 (1988).
Malizewski and Fanslow, Tibtech., 8, 324–329 (1990).
Maniatis, T., Fritsch, E. F. and Sambrook, J., "Molecular Cloning", Cold Spring Harbor Lab. Press, USA (1982).
Neurath, H. and Hill, R. L. in "The Proteins", Academic Press, N.Y., 14 (1979).
Plaetinck et al., J. Exp. Med. 172, 683–691 (1990).
Rolink et al., J. Exp. Med. 169, 1693–1701 (1989).
Sambrook et al., "Molecular Cloning", 2nd ed., Cold Spring Harbor Laboratory Press, USA (1989).
Seed, Nature, 329, 840 (1987).
Seed and Aruffo, Proc. Natl. Acad. Sci. USA, 84, 3365 (1987).
Sharma, S. et al. in "Current Communications in Molecular Biology" edt. by Gething, M. J., Cold Spring Harbor Lab. Press USA (1985).
Traunecker et al., Nature 331, 84–86 (1988).

(List continued on next page.)

*Primary Examiner*—Garnette D. Draper
*Assistant Examiner*—Elizabeth C. Kemmerer
*Attorney, Agent, or Firm*—George M. Gould; George W. Johnston; John P. Parise

[57] ABSTRACT

Chimeric polypeptides encoded by a DNA sequence having a first DNA subsequence coding for a fragment of at least one of the α- and/or β-chain of the human interleukin-5 receptor, and a second DNA subsequence coding for the constant domains of a heavy- or a light-chain of a human immunoglobulin, or a fragment thereof are useful in treating illnesses with demonstrated eosinophilia.

18 Claims, 2 Drawing Sheets

OTHER PUBLICATIONS

Yamaguchi et al., International Immunology 2, 181–187 (1990).

Takaki, S. et al., EMBO Journal, vol. 9, No. 13, pp. 4367–4374 (1990).

Patent Abstracts of Japan—JP-A-10 63 394, vol. 13, No. 262 (1989).

Takaki et al., Lymphokine Research, vol. 9, No. 4, pp. 572–S7.4 (1990).

The Journal of Experimental Medicine, vol. 172, No. 3, pp. 683–691 (1990).

Derwent Abstract No. 91-081851/12.

Derwent Abstract No. 92-009794/02.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1351 base pairs
        ( B ) TYPE: nucleic acid
        ( C ) STRANDEDNESS: single
        ( D ) TOPOLOGY: linear ( i i ) MOLECULE TYPE: cDNA (i i i) HYPOTHETICAL: NO (i v) ANTI-SENSE: NO (v i) ORIGINAL SOURCE:
    (A) ORGANISM: Homo sapiens
    (F) TISSUE TYPE: leukemia
    (G) CELL TYPE: promyelocytes
    (H) CELL LINE: HL-60

(v i i) IMMEDIATE SOURCE:
    (A) LIBRARY: human HL-60
    (B) CLONE: lambda gt11- hIL5Ralpha12

(x i) SEQUENCE DESCRIPTION: SEQ ID NO:1:

```
CCGCTGCTTC TCATCGCATG GCCACCGCAT TTCTCAGGCC AGGCACATTG AGCATTGGTC    60
CTGTGCCTGA CGCTATGCTA GATGCTGGGG TTGCAGCCAC GAGCATAGAC ACGACAGACA   120
CGGTCCTCGC CATCTTCTGT TGAGTACTGG TCGGAACAAG AGGATCGTCT GTAGACAGGC   180
TACAGATTGT TTTAGATTGA AGTTTCCTGT CATGTTCACT CATCTTTAAA TCCTCATAGT   240
AAAAAGGATA TGATCATCGT GGCGCATGTA TTACTCATCC TTTTGGGGGC CACTGAGATA   300
CTGCAAGCTG ACTTACTTCC TGATGAAAAG ATTTCACTTC TCCCACCTGT CAATTTCACC   360
ATTAAAGTTA CTGGTTTGGC TCAAGTTCTT TTACAATGGA AACCAAATCC TGATCAAGAG   420
CAAAGGAATG TTAATCTAGA ATATCAAGTG AAAATAAACG CTCCAAAAGA AGATGACTAT   480
GAAACCAGAA TCACTGAAAG CAAATGTGTA ACCATCCTCC ACAAAGGCTT TTCAGCAAGT   540
GTGCGGACCA TCCTGCAGAA CGACCACTCA CTACTGGCCA GCAGCTGGGC TTCTGCTGAA   600
CTTCATGCCC CACCAGGGTC TCCTGGAACC TCAATTGTGA ATTTAACTTG CACCACAAAC   660
ACTACAGAAG ACAATTATTC ACGTTTAAGG TCATACCAAG TTTCCCTTCA CTGCACCTGG   720
CTTGTTGGCA CAGATGCCCC TGAGGACACG CAGTATTTTC TCTACTATAG GTATGGCTCT   780
TGGACTGAAG AATGCCAAGA ATACAGCAAA GACACACTGG GGAGAAATAT CGCATGCTGG   840
TTTCCCAGGA CTTTTATCCT CAGCAAGGG CGTGACTGGC TTTCGGTGCT TGTTAACGGC    900
TCCAGCAAGC ACTCTGCTAT CAGGCCCTTT GATCAGCTGT TTGCCCTTCA CGCCATTGAT   960
CAAATAAATC CTCCACTGAA TGTCACAGCA GAGATTGAAG GAACTCGTCT CTCTATCCAA  1020
TGGGAGAAAC CAGTGTCTGC TTTTCCAATC CATTGCTTTG ATTATGAAGT AAAAATACAC  1080
AATACAAGGA ATGGATATTT GCAGATAGAA AAATTGATGA CCAATGCATT CATCTCAATA  1140
ATTGATGATC TTTCTAAGTA CGATGTTCAA GTGAGAGCAG CAGTGAGCTC CATGTGCAGA  1200
GAGGCAGGGC TCTGGAGTGA GTGGAGCCAA CCTATTTATG TGGGGTTCTC AAGATAAAGG  1260
AGATAACATC CAGCTTTCCT GCCCCACACC GTATCTGAAA TAAAAACAAC AGCAGGGATA  1320
GCAGATTAAA AAAAAAAAA AAAAAAAAA A                                  1351
```

(2) INFORMATION FOR SEQ ID NO:2:

(i) SEQUENCE CHARACTERISTICS:
        (A) LENGTH: 335 amino acids
        (B) TYPE: amino acid
        (C) STRANDEDNESS: single
        (D) TOPOLOGY: linear (i i) MOLECULE TYPE: protein (i i i) HYPOTHETICAL: YES (i v) ANTI-SENSE: NO (v i) ORIGINAL SOURCE:
        (A) ORGANISM: Homo sapiens (F) TISSUE TYPE: leukemia
        (G) CELL TYPE: Promyelocytes
        (H) CELL LINE: HL-60

(vii) IMMEDIATE SOURCE:
        (A) LIBRARY: human HL-60
        (B) CLONE: lambda gt11- hIL5Ralpha12

(xi) SEQUENCE DESCRIPTION: SEQ ID NO:2:

| Met | Ile | Ile | Val | Ala | His | Val | Leu | Leu | Ile | Leu | Leu | Gly | Ala | Thr | Glu |
| 1 | | | | 5 | | | | | 10 | | | | | 15 | |

| Ile | Leu | Gln | Ala | Asp | Leu | Leu | Pro | Asp | Glu | Lys | Ile | Ser | Leu | Leu | Pro |
| | | | 20 | | | | | 25 | | | | | 30 | | |

| Pro | Val | Asn | Phe | Thr | Ile | Lys | Val | Thr | Gly | Leu | Ala | Gln | Val | Leu | Leu |
| | | 35 | | | | | 40 | | | | | 45 | | | |

| Gln | Trp | Lys | Pro | Asn | Pro | Asp | Gln | Glu | Gln | Arg | Asn | Val | Asn | Leu | Glu |
| | 50 | | | | | 55 | | | | | 60 | | | | |

| Tyr | Gln | Val | Lys | Ile | Asn | Ala | Pro | Lys | Glu | Asp | Asp | Tyr | Glu | Thr | Arg |
| 65 | | | | | 70 | | | | | 75 | | | | | 80 |

| Ile | Thr | Glu | Ser | Lys | Cys | Val | Thr | Ile | Leu | His | Lys | Gly | Phe | Ser | Ala |
| | | | | 85 | | | | | 90 | | | | | 95 | |

| Ser | Val | Arg | Thr | Ile | Leu | Gln | Asn | Asp | His | Ser | Leu | Leu | Ala | Ser | Ser |
| | | | 100 | | | | | 105 | | | | | 110 | | |

| Trp | Ala | Ser | Ala | Glu | Leu | His | Ala | Pro | Pro | Gly | Ser | Pro | Gly | Thr | Ser |
| | | 115 | | | | | 120 | | | | | 125 | | | |

| Ile | Val | Asn | Leu | Thr | Cys | Thr | Thr | Asn | Thr | Thr | Glu | Asp | Asn | Tyr | Ser |
| | 130 | | | | | 135 | | | | | 140 | | | | |

| Arg | Leu | Arg | Ser | Tyr | Gln | Val | Ser | Leu | His | Cys | Thr | Trp | Leu | Val | Gly |
| 145 | | | | | 150 | | | | | 155 | | | | | 160 |

| Thr | Asp | Ala | Pro | Glu | Asp | Thr | Gln | Tyr | Phe | Leu | Tyr | Tyr | Arg | Tyr | Gly |
| | | | | 165 | | | | | 170 | | | | | 175 | |

| Ser | Trp | Thr | Glu | Glu | Cys | Gln | Glu | Tyr | Ser | Lys | Asp | Thr | Leu | Gly | Arg |
| | | | 180 | | | | | 185 | | | | | 190 | | |

| Asn | Ile | Ala | Cys | Trp | Phe | Pro | Arg | Thr | Phe | Ile | Leu | Ser | Lys | Gly | Arg |
| | | 195 | | | | | 200 | | | | | 205 | | | |

| Asp | Trp | Leu | Ser | Val | Leu | Val | Asn | Gly | Ser | Ser | Lys | His | Ser | Ala | Ile |
| | 210 | | | | | 215 | | | | | 220 | | | | |

| Arg | Pro | Phe | Asp | Gln | Leu | Phe | Ala | Leu | His | Ala | Ile | Asp | Gln | Ile | Asn |
| 225 | | | | | 230 | | | | | 235 | | | | | 240 |

| Pro | Pro | Leu | Asn | Val | Thr | Ala | Glu | Ile | Glu | Gly | Thr | Arg | Leu | Ser | Ile |
| | | | | 245 | | | | | 250 | | | | | 255 | |

| Gln | Trp | Glu | Lys | Pro | Val | Ser | Ala | Phe | Pro | Ile | His | Cys | Phe | Asp | Tyr |
| | | | 260 | | | | | 265 | | | | | 270 | | |

| Glu | Val | Lys | Ile | His | Asn | Thr | Arg | Asn | Gly | Tyr | Leu | Gln | Ile | Glu | Lys |
| | | 275 | | | | | 280 | | | | | 285 | | | |

| Leu | Met | Thr | Asn | Ala | Phe | Ile | Ser | Ile | Ile | Asp | Asp | Leu | Ser | Lys | Tyr |
| | 290 | | | | | 295 | | | | | 300 | | | | |

| Asp | Val | Gln | Val | Arg | Ala | Ala | Val | Ser | Ser | Met | Cys | Arg | Glu | Ala | Gly |
| 305 | | | | | 310 | | | | | 315 | | | | | 320 |

| Leu | Trp | Ser | Glu | Trp | Ser | Gln | Pro | Ile | Tyr | Val | Gly | Phe | Ser | Arg | |
| | | | | 325 | | | | | 330 | | | | | 335 | |

(2) INFORMATION FOR SEQ ID NO:3:

(i) SEQUENCE CHARACTERISTICS:
        (A) LENGTH: 335 amino acids
        (B) TYPE: amino acid -continued (D) TOPOLOGY: linear (ii) MOLECULE TYPE: protein (iii) HYPOTHETICAL: YES (vi) ORIGINAL SOURCE:
    (A) ORGANISM: mouse
    (G) CELL TYPE: B-cell precursor
    (H) CELL LINE: B13

(xi) SEQUENCE DESCRIPTION: SEQ ID NO:3:

```
Xaa Xaa Xaa Met Val Pro Val Leu Leu Ile Leu Val Gly Ala Leu Ala
 1           5                   10                  15

Thr Leu Gln Ala Asp Leu Leu Asn His Lys Lys Phe Leu Leu Leu Pro
            20                  25                  30

Pro Val Asn Phe Thr Ile Lys Ala Thr Gly Leu Ala Gln Val Leu Leu
            35                  40                  45

His Trp Asp Pro Asn Pro Asp Gln Glu Gln Arg His Val Asp Leu Glu
     50                  55                  60

Tyr His Val Lys Ile Asn Ala Pro Gln Glu Asp Glu Tyr Asp Thr Arg
 65                  70                  75                  80

Lys Thr Glu Ser Lys Cys Val Thr Pro Leu His Glu Gly Phe Ala Ala
                85                  90                  95

Ser Val Arg Thr Ile Leu Lys Ser Ser His Thr Thr Leu Ala Ser Ser
            100                 105                 110

Trp Val Ser Ala Glu Leu Lys Ala Pro Pro Gly Ser Pro Gly Thr Ser
            115                 120                 125

Val Thr Asn Leu Thr Cys Thr Thr His Thr Val Val Ser Ser His Thr
    130                 135                 140

His Leu Arg Pro Tyr Gln Val Ser Leu Arg Cys Thr Trp Leu Val Gly
145                 150                 155                 160

Lys Asp Ala Pro Glu Asp Thr Gln Tyr Phe Leu Tyr Tyr Arg Phe Gly
                165                 170                 175

Val Leu Thr Glu Lys Cys Gln Glu Tyr Ser Arg Asp Ala Leu Asn Arg
            180                 185                 190

Asn Thr Ala Cys Trp Phe Pro Arg Thr Phe Ile Asn Ser Lys Gly Phe
            195                 200                 205

Glu Gln Leu Ala Val His Ile Asn Gly Ser Ser Lys Arg Ala Ala Ile
    210                 215                 220

Lys Pro Phe Asp Gln Leu Phe Ser Pro Leu Ala Ile Asp Gln Val Asn
225                 230                 235                 240

Pro Pro Arg Asn Val Thr Val Glu Ile Glu Ser Asn Ser Leu Tyr Ile
                245                 250                 255

Gln Trp Glu Lys Pro Leu Ser Ala Phe Pro Asp His Cys Phe Asn Tyr
            260                 265                 270

Glu Leu Lys Ile Tyr Asn Thr Lys Asn Gly His Ile Gln Lys Glu Lys
            275                 280                 285

Leu Ile Ala Asn Lys Phe Ile Ser Lys Ile Asp Asp Val Ser Thr Tyr
    290                 295                 300

Ser Ile Gln Val Arg Ala Ala Val Ser Ser Pro Cys Arg Met Pro Gly
305                 310                 315                 320

Arg Trp Gly Glu Trp Ser Gln Pro Ile Tyr Val Gly Lys Glu Arg
                325                 330                 335
```

(2) INFORMATION FOR SEQ ID NO:4:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:4:

Trp Gly Glu Trp Ser Gln Pro Ile Tyr Val Gly Lys
 1           5                   10

( 2 ) INFORMATION FOR SEQ ID NO:5:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CCHACGTATA THGGCTGHGA CCACTCHCCC CA                                    3 2

( 2 ) INFORMATION FOR SEQ ID NO:6:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

CCHACGTAAA THGGCTGHGA CCACTCHCCC CA                                    3 2

( 2 ) INFORMATION FOR SEQ ID NO:7:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

CCHACATAGA THGGTTGHGA CCATTCHCCC CA                                    3 2

( 2 ) INFORMATION FOR SEQ ID NO:8:

( i ) SEQUENCE CHARACTERISTICS:
        ( A ) LENGTH: 32 base pairs
        ( B ) TYPE: nucleic acid ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

CCHACGTATA THGGCTGACT CCACTCHCCC CA                32

( 2 ) INFORMATION FOR SEQ ID NO:9:

( i ) SEQUENCE CHARACTERISTICS:
         ( A ) LENGTH: 32 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

CCHACGTAAA THGGCTGACT CCACTCHCCC CA                32

( 2 ) INFORMATION FOR SEQ ID NO:10:

( i ) SEQUENCE CHARACTERISTICS:
         ( A ) LENGTH: 32 base pairs
         ( B ) TYPE: nucleic acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CCHACATAGA THGGTTGGCT CCATTCHCCC CA                32

( 2 ) INFORMATION FOR SEQ ID NO:11:

( i ) SEQUENCE CHARACTERISTICS:
         ( A ) LENGTH: 8 amino acids
         ( B ) TYPE: amino acid
         ( C ) STRANDEDNESS: single
         ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

His Val Asp Leu Glu Tyr His Val
      1               5

( 2 ) INFORMATION FOR SEQ ID NO:12:

( i ) SEQUENCE CHARACTERISTICS:
         ( A ) LENGTH: 23 base pairs
         ( B ) TYPE: nucleic acid
         ( C ) STRANDEDNESS: single
         ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:12:

ACATGATATT CTAAATCHAC ATG 23

(2) INFORMATION FOR SEQ ID NO:13:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:13:

ACGTGGTACT CCAAGTCHAC GTG 23

(2) INFORMATION FOR SEQ ID NO:14:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:14:

ACATGATATT CHAGATCHAC ATG 23

(2) INFORMATION FOR SEQ ID NO:15:

(i) SEQUENCE CHARACTERISTICS:
(A) LENGTH: 23 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:15:

ACGTGGTACT CHAGGTCHAC GTG 23

(2) INFORMATION FOR SEQ ID NO:16:

(i) SEQUENCE CHARACTERISTICS:
(A) LENGTH: 28 base pairs
(B) TYPE: nucleic acid
(C) STRANDEDNESS: single
(D) TOPOLOGY: linear (i i) MOLECULE TYPE: cDNA (iii) HYPOTHETICAL: NO (iv) ANTI-SENSE: NO (xi) SEQUENCE DESCRIPTION: SEQ ID NO:16:

AATTCGCGGC CGCTTTTTTT TTTTTTT     28

(2) INFORMATION FOR SEQ ID NO:17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:17:

CTTTAGAGCA CA     12

(2) INFORMATION FOR SEQ ID NO:18:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

CTCTAAAG     8

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

CATAGACACG ACAGACACGG     20

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO ( x i ) SEQUENCE DESCRIPTION: SEQ ID NO:20:

TACTGCAGAT CCGCCTCTTG AGAACCCCAC AT    32

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

AAGCTTGGAT CCATGATCAT CGTGGCGCAT    30

( 2 ) INFORMATION FOR SEQ ID NO:22:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:22:

GAGCTCACCG GATCCGCCTC TTGAGAACCC CACAT    35

DNA ENCODING CHIMERIC POLYPEPTIDES COMPRISING THE INTERLEUKIN-5 RECEPTOR α-CHAIN FUSED TO IMMUNOGLOBULIN HEAVY CHAIN CONSTANT REGIONS

FIELD OF THE INVENTION

The invention is directed to polypeptides and a DNA sequence coding for a fragment of one or both of the α- and/or β-chain of the human interleukin-5 receptor and coding for the constant domains of a heavy- or a light-chain of a human immunoglobulin, or a fragment thereof.

BACKGROUND OF THE INVENTION

Interleukin-5 (IL-5 or IL5) is a lymphokine secreted by T cells and mast cells and biologically activates B cells and eosinophils. The activity on B cells seems to be restricted to the murine system. No detectable activity can be found in a panel of human B-cell activation or differentiation assays. [Clutterbuck et al., Eur. J. Immunol. 17, 1743–1750 (1987)].

In murine hematopoiesis, IL-5 is a selective signal for the proliferation and differentiation of the eosinophilic lineage [Yamaguchi et al., J. Exp. Med. 167, 43–56 (1988)]. In this respect, IL-5 function shows analogies with colony-stimulating factors for other myeloid lineages. Also, human (h) IL-5 is very potent in the activation of human eosinophils [Lopez et al., J. Exp. Med. 167, 219–224 (1988); Saito et al., Proc. Natl. Acad. Sci USA 85, 2288–2292)]. A good discussion of the roles of IL-5 and eosinophils in disease is provided by Sanderson, C. J., Blood, Vol. 79, No. 12 (June 15), 1992, pp. 3101–3109.

Interleukin 5 mediates its activity through a cell membrane receptor-complex. This complex has been characterized physicochemically in both the murine and human system. Mouse pre B cell lines depending on IL5 for their growth have been developed from bone marrow and are used for IL5-receptor analysis [Rolink et al., J. Exp. Med. 169, 1693–1701 (1989)]. The human IL5-receptor (hIL-5R) can be studied on a subclone of the promyelocytic cell line HL60 induced towards eosinophil differentiation [Plaetinck et al., J. Exp. Med. 172, 683–691 (1990)].

Eosinophilic differentiation is initiated using sodium butyrate. Only high affinity (Kd=30 pM) IL5 binding sites can be found on these cells. However cross-linking studies reveal the presence of two polypeptide chains of the receptor involved in IL5 binding, with molecular masses closely resembling the murine IL5R-α- and -β chains.

Increased half-life in vivo has been shown for example, for chimeric polypeptides consisting of the first two domains or parts thereof of the human CD4-molecule and different domains of the constant regions of the heavy chain or the light chain of a mammalian immunoglobulin (see Traunecker et al., Nature 331, 84–86 [1988] and European Patent Application 90107393.2, Publication No. 394,827).

The specification of European Patent Application 90107393.2, which is the relevant portions of which are described latter in the specification, contains data with respect to the use of pSV-2-derived vectors for the expression of chimeric proteins as well as the construction of vectors for the expression of such chimaeric proteins with other immunoglobulin fragments.

As described above, sources for DNA sequences coding for constant domains of human immunoglobulins are known in the state of the art and disclosed, for example, in EP 394,827 or are described for example by Ellison et al., Nucl. Acid Res. 10, 4071–4079 (1982) for IgG1, or Huck et al., Nucl. Acid Res. 14, 1779–1789 (1986) for IgG3.

SUMMARY OF THE INVENTION

The invention is directed to a DNA sequence which comprises a combination of two DNA subsequences, with one of the subsequences coding for a fragment of the α- and/or the β-chain of the hIL5R. The hIL5R fragment, or combination of fragments, is capable of binding hIL-5, and the other subsequence codes for part or all constant domains of the human immunoglobulin heavy- or light-chains.

The invention additionally pertains to vectors comprising such DNA sequences, especially such vectors capable of expression in eukaryotic host cells. The invention also relates to prokaryotic or eukaryotic host cells transformed with such vectors.

The present invention is also concerned with the recombinant chimeric polypeptides coded by such DNA sequences, as well as their use, especially for the treatment of illnesses having demonstrated eosinophilia, for example chronic asthma, and helmith infections. A soluble human IL5Rα-chain (shIL5Rα) would be advantageous as an IL-5 antagonist in chronic asthma or other disease states with demonstrated eosinophilia. In addition the shIL5Rα or the α-chain itself or the whole high affinity receptor, consisting of the α-chain and the β-chain [Tavernier et al., Cell 66, in press (1991)] could be used as a tool for screening for IL-5 antagonists. Of course, the invention also includes such proteins in which the amino acid sequences are deleted or exchanged, so that the activity of the proteins is not significantly altered. Amino acid exchanges in proteins and peptides which do not generally alter the activity of such molecules are known in the state of the art and are described, for example, by H. Neurath and R. L. Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, Asp/Gly as well as these in reverse.

Figure 1:
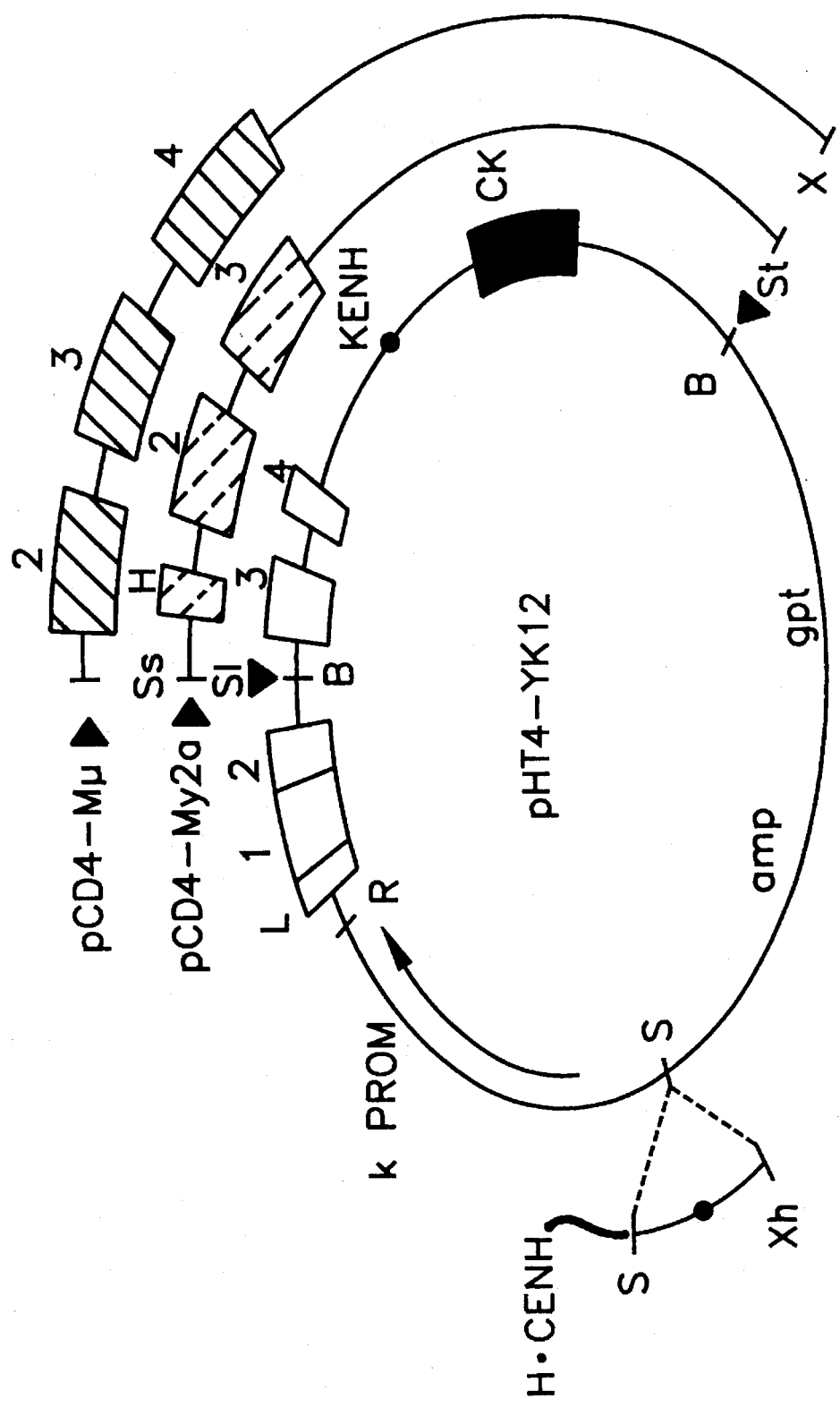
FIG. 1 shows the plasmids pHT4-YK12, pCD4Mμ and pCD4-Mγ2a. Boxes refer to pieces of cDNA equivalent to specific parts of exons [see Example 14] or exons themselves used for the construction of the plasmids wherein the white boxes refer to DNA coding for the leader region (L) and all four (1,2,3,4) extracellular domains of the human CD4-molecule. The black box refers to the exon coding for the immunoglobulin κ light-chain constant region (cκ). The dotted boxes refer to the exons coding for the hinge (H) and the second and third domains of the mouse IgG$_{2a}$ constant regions (C2, C3) respectively. The striped boxes refer to the exons coding for the second, third and fourth domains for the mouse IgM constant regions respectively. Further abbreviations refer to: B=BamHI restriction site, R=EcoRI restriction site, S=SalI restriction site, Ss=SstI restriction site, St=StuI restriction site, X=XbaI restriction site, Xh=XhoI restriction site, amp=ampicillin resistance gene, gpt=E. Coli xanthine-guanine phosphoribosyltransferase gene, κ prom= Igκ promotor, κENH=Igκ enhancer, H•CENH=Ig heavy chain enhancer.

Hμ and pCD4-Hγ1. In these latter plasmids, the boxes represent the human IgG and IgM regions corresponding to the mouse exons of FIG. 1. "P" refers to a PstI restriction site and "Ha" to a HaeII restriction site, "PV" to a PVuII restriction site and "Sm" to a SmaI restriction site. All other symbols and abbreviations have the same meaning as in FIG. 1.

DETAILED DESCRIPTION OF THE INVENTION

The invention is directed, in part, to a DNA sequence which comprises a combination of two DNA subsequences, with one of the subsequences coding for a fragment of the α- and/or the β-chain of the hIL5R. The hIL5R fragment, or combination of fragments, is capable of binding hIL5, and whereby a fragment of the soluble hIL5Rα-chain (shIL5Rα) and especially such a fragment with the whole or a part of the sequence as shown in SEQ ED NO. 1 is preferred. The other subsequence codes for constant domains of the human immunoglobulin heavy- or light-chains. The heavy chains, especially all domains except the first domain of the constant domain of human immunoglobulins such as IgG, IgA, IgM or IgE and specifically IgG, for example IgG1 and IgG3 are preferred.

It is furthermore understood that a DNA sequence coding for a fragment of the α-chain of the hIL5R which fragment binds hIL5 comprises also DNA sequences which hybridize under stringent hybridization conditions to a DNA sequence as shown in SEQ ID NO. 1 which DNA sequence codes for a protein which is capable of binding hIL5. A man skilled in the art will easily be able to define such stringent hybridization conditions based on the DNA-sequence shown in FIG. 1 and according to standard knowledge in the state of the art and disclosed for example in Sambrook et al. "Molecular Cloning", 2nd. ed., Cold Spring Harbor Laboratory Press (1989). The DNA sequences of the invention also comprise DNA sequences which hybridize to the DNA sequence which is complementary to the DNA sequence shown in SEQ ID NO. 1. In addition, the DNA sequence which codes for a fragment of the α-chain of the hIL5R fragment which fragment is capable of binding hIL5 also comprises DNA sequences which, because of the degeneracy of the genetic code, do not hybridize with the sequence SEQ ID NO. 1, or its complement, but which code for polypeptides having exactly the same amino acid sequence as the fragment of the α-chain of the human IL5R.

It is furthermore understood that for the purpose of the present invention the chimeric polypeptides can be in a dimeric form, namely consisting either of two subunits whereby each subunit comprises a fragment of the α-chain of the IL5R which binds hIL5 or of two subunits whereby one of the two subunits comprises a fragment of the α-chain of the IL5R and the other subunit comprises a fragment of the β chain of the IL5R so that the dimeric polypeptide binds hIL5.

Cloned DNA can be obtained in the form of genomic DNA isolated from a genomic library by methods well known in the art and described for example by Maniatis, T., et al. in "Molecular Cloning." For example, specific oligonucleotide probes can be prepared on the at least partial knowledge of the amino acid sequence encoded by the specific genomic DNA (exons) to be isolated or the at least partial knowledge of its nucleic acid sequence. Such sequence information can be obtained in principle from any sequence data base, for example, Genbank (Intelligenetics, California, U.S.A.), EMBL (Heidelberg, FRG), NBRF (Georgetown University, Medical Centre, Washington, DC, U.S.A.) and Vecbase (University of Wisconsin, Biotechnology Centre, Madison, Wis., U.S.A.), or more specifically, for example, for the human Ig μ from Rabbits, T. H., et al., *Nucleic Acids Res.*, 9:4509–4524 (1981); for the human IgY1 from Ellison, J. W., et al., *Nucleic Acids Res.*, 10: 4071–4079 (1982); for the human Ig γ3 heavy chain gene from Huch, S., et al., *Nucleic Acids Res.*, 14:1779–1789 (1986); and for the human Igα1 and Igα2 heavy chain gene from Flanagan, J. G., et al., *Cell*, 36:681–688 (1984).

The cloning of a DNA sequence coding for the α-chain of the hIL5R can be achieved in the following manner. Murine cell lines which contain the murine IL-5-receptor (mIL5R) in membrane-bound form, can be cultivated according to methods known in the art or as specifically described, for example, in Example 2. Such cells can then be harvested by centrifugation, lysed and a membrane extract can be prepared by using a suitable detergent, for example Triton-X-100. For the isolation of the α-chain of mIL5R, the membrane extract, cleared by centrifugation, can be passed over an immuneaffinity matrix. The corresponding antibodies for such an immunematrix namely the ones to the α-chain of the mIL5R can be prepared and coupled to an appropriate matrix by methods well known in the art or as specifically described, for example, in Examples 1–3. The α-chain of the mIL5R can be further purified by sodium dodecylsulfate polyacrylamide gelectrophoresis (SDS-PAGE) and blotted to an appropriate matrix.

The thus-purified murine IL-5-receptor chain can be characterized by methods of peptide chemistry which are known in the state of the art, such as, for example, N-terminal amino acid sequencing or enzymatic as well as chemical peptide cleavage. Fragments obtained by enzymatic or chemical cleavage can be separated according to usual methods such as, for example, HPLC and can themselves be subjected to further N-terminal sequencing.

Starting from the so-obtained amino acid sequence information, oligonucleotides can be produced according to methods known in the state of the art [see, for example, Sambrook et al., supra] taking into consideration the degeneration of the genetic code.

cDNA or genomic DNA libraries can be produced according to methods known in the art [Sambrook et al. supra.], whereby cDNA libraries on the basis of an mRNA-preparation from cell lines expressing with or without induction murine or human IL5R, for example as specifically described in Example 4, are preferred. Such libraries can then be screened by oligonucleotides [Sambrook et al., supra]. Once a specific clone has been identified in such a manner, the phage harboring the desired DNA sequence of the invention can be isolated [Sambrook et al., supra] and the corresponding inserts characterized by restriction enzyme cleavage pattern analysis or sequencing according to standard procedures [Sambrook et al., supra]. It is understood that DNA sequences hybridizing under stringent hybridization conditions to those of the present invention and coding for proteins which bind IL5 can be employed for the purpose of the present invention. Such DNA sequences can be prepared for example by mutagenesis methods known in the art [see, for example, Sambrook et al., supra] starting from the corresponding non-mutated DNA sequences. Furthermore, the well-known polymerase chain reaction (PCR) can be used for the preparation of DNA sequences of the present invention as described in detail in examples 12 and 13. Stringent hybridization conditions can be determined by a man skilled in the art by standard procedures as given, e.g. by [Sambrook et al., supra].

On the basis of the thus-determined DNA sequences and of the already known DNA sequences for certain receptors, those partial DNA sequences which code for a soluble receptor subunit can be determined and cut out from the complete DNA sequence using known methods, see Sambrook et al., supra and Maliszewski and Fanslow, Tibtech., 8, 324–329 (1990).

The complete DNA sequence or such partial DNA sequences can then be integrated using known methods into expression vectors described in the state of the art for their amplification and/or expression in prokaryotes [Sambrook et al., supra]. Suitable prokaryotic host organisms are, for example, gram-negative and gram-positive bacteria such as, for example, *B. subtilis* strains or *E. coli* strains such as *E. coli* HB 101 [ATCC No. 33 694] or *E. coli* W3110 [ATCC No. 27 325] and *E. coli* MC1061 [Casadabam and Cohen, J. Mol. Biol. 138, 179–207 (1980)]. The latter two harboring plasmid "p3" ]Sambrook et al., supra] in case the pCDM8-type vectors like τVX or pshIL5Rα. (See Example 9) will be amplified.

Furthermore such DNA sequences can be integrated using known methods into suitable vectors for expression in eukaryotic host cells, such as, for example, yeast, insect cells and mammalian cells.

A typical expression vector for mammalian cells contains an efficient promoter element in order to produce a good transcription rate of the DNA. Also included in the vector is the DNA sequence to be expressed, and DNA coding signals for an efficient termination and polyadenylation of the transcript. Additional elements which can be used are "enhancers" which lead to again intensified transcription, and sequences which for example can bring about a longer half life of the mRNA. For the expression of nucleic acid sequences in which the endogenous sequence fragment coding for a signal peptide is missing, there can be used vectors which contain such suitable sequences which code for signal peptides of other known proteins. See, for example, the vector pLJ268 described by Cullen, B. R. in Cell 46, 973–982 (1986) as well as Sharma, S. et al. in "Current Communications in Molecular Biology", edt. by Gething, M. J., Cold Spring Harbor Lab. (1985), pages 73–78.

Most of these vectors which are used for a transient expression of a particular DNA sequence in mammalian cells contain the replication origin of the SV40 virus. In cells which express the T-antigen of the virus (for example COS cells), these vectors are reproduced abundantly. A transient expression as described for example in Example 10 is, however, not limited to COS cells. In principle, any transfectable mammalian cell line can be used for this purpose. Signals which can bring about a strong transcription are for example the early and late promoters of SV40, the promoter and enhancer of the "major immediate-early" gene of HCMV (human cytomegalovirus), the LTR's ("long terminal repeats") of retroviruses such as, for example, RSV, HIV and MMTV. There can, however, also be used signals of cellular genes such as for example the promoters of the actin and collagenase genes.

Alternatively, however, stable cell lines which have the specific DNA sequence integrated into the genome (chromosome) also are suitable. For this, the DNA sequence is contransfected together with a selectable marker, for example neomycin, hygromycin, dihydrofolate reductase (dhfr) or hypoxanthin guanine phosphoribosyl transferase (hgpt) using methods which are per se known in the art. The DNA sequence stably incorporated in the chromosome can also be amplified abundantly. A suitable selection marker for this is, for example, dihydrofolate reductase (dhfr). Mammalian cells, for example, chinese hamster ovary (CHO) cells, which contain no intact dhfr gene, are thereby incubated with increasing amounts of methotrexate after transfection has been effected. In this manner cell lines which contain more than a thousand copies of the desired DNA sequence can be obtained.

Mammalian cells which can be used for expression are for example cells of the human cell lines Hela [ATCC CCL2] and 293 [ATCC CRL 1573] as well as 3T3 [ATCC CCL 163] and L cells, for example [ATCC CCL 149], (CHO) cells [ATCC CCL 61], BHK [ATCC CCL 10] cells as well as the CV 1 [ATCC CCL 70] and the COS cell lines [ATCC CRL 1650, CRL 1651].

Suitable expression vectors include, for example, vectors such as pBC12MI [ATCC 67 109], pSV2dhfr [ATCC 37 146], pSVL [Pharmacia, Uppsala, Sweden], pRSVcat [ATCC 37 152], pMSG [Pharmacia, Uppsala, Sweden] and pCDM8 type plasmids like for example pshIL5Rα [see Example 7] which has been deposited transformed in *E.coli* MC1061 (harboring plasmid p3) under the conditions of the Budapest Treaty for patent purposes at the Deutsche Sammlung von Mikroorganismen und Zellkulturen GmbH (DSM) in Braunschweig, Federal Republic of Germany on Apr. 17, 1991 under accession number DSM 6479. The plasmid pshIL5Rα can be isolated from the deposited transformed *E.coli* as known in the art and described for example in detail in Example 9.

For the expression of the chimeric polypeptides of the present invention, there can be used pSV2-derived vectors [see for example German, C. in "DNA Cloning" Vol. II., edt. by Glover, D. M., IRL Press, Oxford, 1985] like pCD4-Hµ (DSM 5315), pCD4-Hγ1 (DSM 5314) and pCD4-Hγ3 (DSM 5523) which have been deposited at the Deutschen Sammlung von Mikro-organismen und Zellkulturen GmbH (DSM) in Braunschweig, FRG, and which are described in detail in European Patent Application No. 90107393.2, Publication No. 394,827. For the purpose of the present invention, the CD4 coding part in the vectors of the EPA application must be replaced by a DNA sequence coding for a fragment of the α- and/or β-chain of the hIL5R which binds hIL5. The replacement of the CD4 region with the hIL5R fragment is performed by methods known per se in the art and described for example in Sambrook et al., supra. If desirable, the specific immunoglobulin coding region in the vectors obtained also can be replaced by a DNA sequence coding for the desired immunoglobulin. Preferred vectors for the expression of the chimeric polypeptides of the present invention are pCDM8 type vectors like for example pshIL5Rα for the expression of fragments of the α-chain of the IL5R containing chimeric polypeptides (see examples 12 and 13).

The manner in which these cells are transfected depends on the chosen expression system and vector system. An overview of these methods is to be found, for example, in Pollard et al., "DNA Transformation of Mammalian Cells" in "Methods in Molecular Biology", Nucleic Acids Vol. 2, 1984, Walker, J. M., ed, Humana, Clifton, N.J. Further methods are to be found in Chen and Okayama "High-Efficiency Transformation of Mammalian Cells by Plasmid DNA", Molecular and Cell Biology 7, 2745–2752, 1987 and in Felgner Felgner et al., "Lipofectin: A highly efficient, lipid-mediated DNA-transfection procedure", Proc. Nat. Acad. Sci. USA 84, 7413–7417, 1989.

The baculovirus expression system, which has already been used successfully for the expression of a series of proteins (for an overview see Luckow and Summers, Bio/Technology 6, 47–55, 1988), can be used for the expression in insect cells. Recombinant proteins can be produced in authentic form or as fusion proteins. The thus-produced proteins can also be modified such as, for example, glycosylated (Smith et al., Proc. Nat. Acad. Sci. USA 82, 8404–8408, 1987). For the production of a recombinant baculovirus which expresses the desired protein there is used a so-called "transfer vector". Under this there is to be understood a plasmid which contains the heterologous DNA sequence under the control of a strong promoter, for example that of the polyhedron gene, whereby this is surrounded on both sides by viral sequences. The transfer vector is then transfected into the insect cells together with DNA of the wild type baculovirus. The recombinant viruses which result in the cells by homologous recombination can then be identified and isolated according to known methods. An overview of the baculovirus expression system and the methods used therein is to be found in Luckow and Summers, "A Manual of Methods for Baculovirus Vectors and Insect Cell Culture Procedures", Texas Agricultural Experimental Station, Texas A & M University, Bulletin No. 1555, 2nd edition, 1988. It is understood that for the practice of the present invention when using the baculovirus expression system, DNA-sequences coding for the immunoglobulin part have to be in the form of a cDNA.

The chimeric polypeptides of the invention can then be purified from the cell mass or the culture supernatants according to methods of protein chemistry which are known in the state of the art, such as, for example, precipitation for example with ammonium sulfate, dialysis, ultrafiltration, gelfiltration, ion-exchange chromatography, SDS-PAGE, isoelectric focusing, affinity chromatography like immunoaffinity chromatography, HPLC in normal or reverse phase systems or the like.

The chimeric polypeptides of the invention as well as their physiologically compatible salts, which can be manufactured according to methods which are known in the state of the art, can also be used for the treatment of illnesses in which IL-5 is involved in their course and/or the production of corresponding pharmaceutical preparations. For this purpose, one or more of the compounds, where desired or required in combination with other pharmaceutically active substances, can be processed in a known manner with the usually used solid or liquid carrier materials. The dosage of such preparations can be effected having regard to the usual criteria in analogy to already used preparations of similar activity and structure. Such pharmaceutical preparations and the use of the compounds of the present invention for therapeutical purposes are also an object of the present invention.

The following Examples are intended to illustrate details of the invention, without thereby limiting it in any manner. Unless indicated otherwise, the Examples were carried out as written. Unless indicated otherwise, all methods used below are standard methodology according to Sambrook et al. (1989), Molecular Cloning. A Laboratory Manual (2nd edn). Cold Spring Harbor, N.Y., Cold Spring Harbor Laboratory Press.

EXAMPLE 1

Production of Monoclonal Antibodies Against the Murine IL5R

Immunization was carried out generally as described by A. Rolink et al., J. Exp. Med., 169, 1693–1701 (1989). That is, at day 0, $2 \times 10^7$ B13 cells (Rolink et al., supra) were washed with phosphate buffered saline (PBS-A), mixed with complete Freund's adjuvant (CFA) and injected into the hind footpath of Wistar rats. This was repeated without Freund's adjuvant (FA) on day 5 and 7. On day 8, regional lymph nodes were removed and a cell suspension was prepared. These cells were fused using PEG 1500 (Boehringer) with Sp2/0-Ag14 cells [ATCC CRL 1581] at a ratio of 5:1:5. Cells were plated in microtiterplates in the presence of 500 pg/ml of recombinant hIL-6 [Haegemann et al., Europ. J. Biochem. 159, 625–632 (1986)]. The next day, the same volume of medium containing a 2× conc. of aminopterin was added for selection of hybrid cells. Cells were refed at day 8 with medium without aminopterin. Hybridomas were selected on the ability of their supernatant to inhibit the mIL5 [Tavernier, J. et al., DNA 8, 491–501 (1989)] or a mouse interleukin-3 (mIL3) driven proliferation of B13 cells (measured by a $^3$Hdeoxy-cytidin incorporation assay as known in the art). Conditioned medium from WEHI-3 cells (ATCC No. TIB68) was used as a source of mIL3. Supernatants demonstrating inhibiting activity were retested in a competition-binding assay with radiolabeled (according to methods known in the art) mIL5 or "R52" ( a monoclonal antibody recognizing only the β-chain of the IL-5-R, see Rolink et al., supra) on B13 cells. Monoclonal antibodies directed only to the α-chain of the mIL-5-R were identified on their ability to almost completely inhibit mIL5 binding and by immunprecipitation of the corresponding mIL-5-R chain. Selected hybridomas were recloned by the well-known limiting dilution method.

EXAMPLE 2

Immunoaffinity purification of the mIL5R-β-chain

B13 cells were grown in large spinner flasks in Iscove's modified Dulbecco's medium (Gibco Laboratories, Grand Island N.Y., USA) containing 5% fetal calf serum, 2 mM L-glutamine, 50 µg/ml gentamycin, and 100 units/ml recombinant mouse IL-5, to a density of $2 \times 10^6$ cells/ml. Cells from 10 l cultures were concentrated by centrifugation, washed with PBS and lysed in 200 ml PBS containing 1% Triton-X-100 and a cocktail of protease inhibitors (1 mM PMSF, 10 mM benzamidine.HCl, 100 U/ml aprotinin). After 10 min on ice, the lysate was centrifuged for 10 min at 1000×g and cleared by ultracentrifugation (100.000×g) for 90 min at 4° C. The supernatant was diluted with NaCl to a final concentration of 0.5M, and used for purification. "R52" was covalently bound to protein G-Sepharose 4 Fast Flow (Pharmacia, LKB Biotechnology AB, Uppsala, Sweden) according to Schneider et al. [J. Biol. Chem. 257, 10766 (1982)], at a concentration of 5 mg/ml gel. Two hundred ml lysate of B13 cells was passed at 4° C. over 2 ml protein G-Sepharose 4 Fast Flow followed by 2 ml R52-linked protein G-Sepharose 4 Fast Flow both packed in a 1 cm diameter column. The flow through was then reloaded on both columns. The gel was washed extensively (100 ml) with a buffer containing 50 mM Tris-HCl (pH 8.2), 1 mM EDTA, 0.5M NaCl, 0.5% NP40, followed by 10 ml 0.1% (NP40). Next, the retained proteins were eluted in 4 ml 50 mM diethylamine (pH11) containing 0.1% Nonidet P40 (NP40), neutralized by addition of 1M $NaH_2PO_4$ and concentrated by lyophilization. The purity was assessed by SDS-PAGE and Coomassie staining of 2.5% of the eluate.

EXAMPLE 3

Immunoaffinity purity of the murine IL5R α-chain

B13 cell lysates from $2 \times 10^{10}$ cells (run through fractions of the "R52"-immunoaffinity column used to purify the β-chain doublet according to Example 2) were mixed overnight by 4° C. with 2 ml hydrazide avidgel AX (Bioprobe Int. Inc.) armed with 10 mg mAbs recognizing the mIL5R α-chain. The gel was then poured into a column, and after extensive washing (50 mM Tris.HCl, pH 8.2, 1 mM EDTA, 0.5M NaCl, 0.5% NP40; followed by 0.1% NP40 in $H_2O$) elution was performed using 50 mM diethylamine, pH 11, 0.01% NP40. Selected fractions were immediately lyophilized and resuspended in 2× Laemmli buffer, in the presence of β-mercaptoethanol. Samples were run through a 1.5 mm 10% PAGE-SDS gel. The gel was fixed in 10% HAc, 30% methanol and stained with Coomassie Brilliant Blue. Slices containing the 60 kDa mIL5R α-chain were treated with SDS buffer, sliced further and electrophoresed in a new PAGE-SDS gel.

After transfer to an Immobilon-P membrane (Millipore Corp.), and staining with amido black, the 60 kDa band was excised and in situ digested with trypsin. Peptides were separated on a C4-reversed-phase column and subjected to sequence analysis using a 470A-type gas-phase sequenator equipped with an on-line 120A-type PTH-amino acid analyser (Applied Biosystems Inc., Foster City, Calif). Amino Amino acid sequences (standard abbreviations of amino acids) and the sequences of corresponding sets of oligonucleotide probes, synthesized according to methods known in the art, are shown below:

TCGCGGCCGC(T)$_{15}$-3' [SEG ID NO: 16], Promega Corp.) and cloned Moloney Murine Leukemia Virus RNaseH⁻ Reverse Transcriptase (BRL Life Technologies, Inc.). EcoR1 linkered double stranded cDNA was made using described procedures [Sambrook et al., supra]. Not1 cleavage was used to generate a unique 3' sticky-end, and cDNAs were size selected (>1.000 bp) on a 1% agarose gel. After elution using the "gene clean" protocol (BIO 101 Inc.), cDNAs were ligated into the EcoR1-Not1 arms of the λgt11 Sfi-Not vector (Promega Corp.). After in vitro packaging, around $40 \times 10^6$ recombinant phages were obtained.

2. Human, HL60 clone (butyrate induced) cDNA library

Prior to mRNA purification, butyrate induced HL60 clone 15 cells [Fischkoff, Leukemia Res. 12, 679–686 (1988); Plaetinck et al., J. Exp. Med. 172, 683–691 (1990); HL60: ATCC-No. CCL 240] were checked for proper $^{125}$I-hIL5 binding (around 2000 binding sites per cell). The same protocols as for the murine pre-B cell B13 cDNA library, above, were used, and a comparable yield of recombinant phage was obtained.

peptide 1

```
1 2 3 4 5 6 7 8 9 10 11 12
W G E W S Q P I Y V G K        [SEQ ID NO: 4]
``` oligonucleotide-set 1 : 32-mers

```
              T                                            [SEQ ID NO: 5]
5' CC IAC GTA AAT IGG CTG IGA CCA CTC ICC CCA 3'           [SEQ ID NO: 6]
        A   G         T       T                            [SEQ ID NO: 7]

T                                            [SEQ ID NO: 8]
5' CC IAC GTA AAT IGG CTG ACT CCA CTC ICC CCA 3'           [SEQ ID NO: 9]
        A   G         T   G   T                            [SEQ ID NO: 10]
``` peptide 2

```
1 2 3 4 5 6 7 8
H V D L E Y H V       [SEQ ID NO: 11]
``` oligonucleotide-set 2 : 23-mers

```
5' AC ATG ATA TTC TAA ATC IAC ATG 3'     [SEQ ID NO: 12]
      G   G   C   C   G       G          [SEQ ID NO: 13]

5' AC ATG ATA TTC IAG ATC IAC ATG 3'     [SEQ ID NO: 14]
      G   G   C       G       G          [SEQ ID NO: 15]
```

EXAMPLE 4

Construction of unidirectional λGT11 cDNA libraries

1. Murine pre-B cell B13 cDNA library mRNA was extracted from B13 cells using the "fast-track" mRNA isolation system (Invitrogen Corp.). Using this protocol, poly(A)⁺ mRNA was directly isolated from cell lysates using oligo(dT) cellulose; yields were around 50 μg per $10^8$ cells. 5 mg poly(A)⁺ mRNA was reverse transcribed using an oligo dT-Not1 primer-adaptor (5'-AAT-

EXAMPLE 5

Screening of murine and human cDNA libraries

Two sets of oligonucleotide probes "Oligonucleotide 1" and "Oligonucleotide 2", see Example 3, were used for screening under different hybridization conditions, dependent on the type of probe used, by methods known in the art [Sambrook et al., supra]. Results are presented in the scheme below:

1. Two cDNA clones (λgt11-mIL5Rα2,3) were selected from part of the murine cDNA library ($1.2 \times 10^6$ plaques were screened), on the basis of hybridization with both sets of oligonucleotide probes. For that purpose, plaque lifts were prepared as described using Biodyne A transfer membranes (Pall), [Sambrook et al., supra]. Oligonucleotide 1 was radioactively labeled by kinasing [Sambrook et al., supra] and was hybridized under "intermediate stringency" hybridization conditions, as described below. Oligonucleotide 2 was radioactively labeled by kinasing [Sambrook et al., supra] and was hybridized under "low stringency" hybridization conditions as described below.

2. One cDNA clone (λgt11-hIL5Rα8) was selected from part of the human cDNA library (2.4×10$^6$ plaques were screened), on basis of hybridization with both "oligonucleotide 1" and the cDNA insert, which was derived by methods known in the art, from the murine λgt11mIL5Rα2.

Oligonucleotide 1 was radioactively labeled by kinasing [Sambrook et al., supra] and was hybridized under "low stringency" hybridization conditions. The cDNA insert form λgt11mIL5Rα2 was radioactively labeled by random labeling [Sambrook et al., supra] and was hybridzed under "intermediate stringency" hybridization conditions.

3. Five additional cDNA clones (λgt11-hIL5Rα11→15) were selected from half of the human cDNA library screened as in 2. above, using the mIL5Rα2 cDNA probe. Hybridization was under "intermediate stringency" conditions.

4. Thirty-six additional cDNA clones (λgt11-hIL5Rα16→51) were selected from the other half of the human cDNA library screened as in 2. above using the hIL5Rα8-cDNA probe. Hybridization was under "high stringency" conditions as described below.

---

Hybridization conditions

"Low Stringency" Hybridization Conditions:

prehybridization: 5 x SSC (citrate buffered salt
solution known in the art, see for example Sambrook et al.),
5x Denhardt's, 0.1% SDS, 0.05% sodium
pyrophosphate, 100 μg/ml sonicated salmon sperm DNA;
overnight at 42° C.
hybridization: prehybridization buffer was replaced by
the same buffer but including the radioactively
labeled probe.
washes: 4 consecutive washes (around 30 min. each)
with 2x SSC, 0.1% SDS at 37° C.:
"Intermediate Stringency" Hybridization Conditions:

rehybridization: 20% formamide, 5x SSC, 5x
Denhardt's, 5 mM EDTA, 25 mM sodium phosphate (pH 6.5),
0.05% sodium pyrophosphate, 100 μg/ml sonicated
salmon sperm DNA; overnight at 42° C.
hybridization: prehybridization buffer was replaced by
the same buffer but including the radioactively
labeled probe.
washes: 4 consecutive washes (around 30 min. each)
with 2x SSC, 0.1% SDS at 37° C.
"High Stringency" Hybridization Condition prehybridization: 6x SSC, 5x Denhardt's, 0.5% SDS, 100
μg.ml$^{-1}$, sonicated salmon sperm DNA, overnight at
68° C.
hybridization: 6x SSC, 5x Denhardt's, 0.5% SDS, 5 mM
EDTA, 100 μg..ml$^{-1}$ sonicated salmon sperm DNA
including the radioactively labeled probe.
washes: the following consecutive washes (around 30
min. each) were performed: - 2x SSC, 0.1% SDS at room
temperature (twice); and 0.1x SSC, 0.1% SDS at 68° C.
(twice).

---

EXAMPLE 6

Sequencing

All cDNAs were subcloned in pGEM7zf type vectors (Promega Corp.), and Exo III deletion mutants have been generated according to methods known in the art. Sequencing was performed using a protocol based on the Sanger procedure and involving Taq polymerase and single stranded DNA on an automated 37OA DNA Sequencer.

EXAMPLE 7

Construction of plasmid "pshIL5Rα"

Plasmid constructions were carried out as described in the following paragraphs. Unless indicated otherwise, all methods used below are standard methodology according to Sambrook et al. (1989), Molecular Cloning. A Laboratory Manual (2nd edn). Cold Spring Harbor, N.Y., Cold Spring Harbor Laboratory Press.

The insert from phage λgt11-hIL5Rα12 (see Example 5) was excised using EcoR1 and Not1 restriction enzymes. Both sticky ends were filled in using *E.coli* DNA polymerase 1 Klenow fragment in the presence of all four deoxynucleotide triphosphates, and non-palindromic BstX1 linkers were added using T4 DNA ligase. The sequence of these linkers is as follows:

5' CTTTAGAGCACA 3'[SEQ ID NO: 17].

3' GAAATCTC 5'. [SEQ ID NO: 18].

In the next step, the modified insert was ligated into plasmid pCDM8, see, Seed and Aruffo, Proc. Natl. Acad. Sci. U.S.A., 84, 3365 (1987); Aruffo and Seed, Proc. Natl. Acad. Sci. U.S.A., 84, 8573 (1987); and Seed, Nature, 329, 840 (1987); and the construct with the appropriate orientation versus the CMV-promoter was chosen for further analysis.

EXAMPLE 8

Transformation of *E.coli* MC1061(p3)

Transformation of *E.coli* MC1061 (p3) with the plasmid pshIL5Rα of Example 7 was achieved by the electroporation procedure. A Gene Pulser from Bio-Rad (Richmond, Calif., U.S.A.) was used in accordance with manufacturer's instructions, with settings at: 25 μF, 2.5 kV and 200 Ohms.

EXAMPLE 9

Isolation of Plasmid DNA

Plasmid DNA from transformed *E. coli* MC1061, as described in Example 8, was prepared using a standard procedure Birnboim and Doly, Nucl. Acids Res. 7, 1513 (1979); and Sambrook et al., 1989) based upon alkali lysis of the cells, followed by a cesium-chloride ultracentrifugation step. In this way plasmid pshIL5Rα was separated from plasmid p3. The insert coding for shIL5Rα was cut out of pshIL5Rα and sequenced as described in Example 6. The complete nucleic acid sequence and the deduced amino acid sequence of the shIL5Rα are shown in SEQ ID NO: 1 and SEQ ID NO: 2, respectively. SEQ ID NO: 3 is the corresponding amino acid sequence of the murine IL5Rα.

EXAMPLE 10

Expression of shIL5Rα in COS-1 cells

COS-1 cells were transfected using the DEAE-Dextran protocol as described in Sambrook et al., 1989. Subconfluent COS-1 cells were harvested by trypsinization and replated at $2.3 \times 10^4$ cells/cm$^2$, 24 hours prior to transfection. The monolayers were washed twice with minimal essential medium (MEM)-Hepes pH 7.2 and incubated for 30 minutes with the transfection mixture [10 μg pshIL5Rα isolated as described in Example 9/ 0.5 mg DEAE-dextran ($M_r = 2 \times 10^6$; Pharmacia, Uppsala, Sweden)/ml MEM-Hepes, pH 7.2]. Next the cells were supplemented with 8 volumes prewarmed Dulbecco's modified Eagles medium (DMEM) containing 10% foetal calf serum (FCS) and 100 μM chloroquine diphosphate, and incubated for 4 hours at 37° C. Thereafter the medium was removed by aspiration and the monolayers were washed once with DMEM and incubated for 3 days in DMEM+10% FCS.

EXAMPLE 11

Characterization of shIL5Rα

Figure 2:
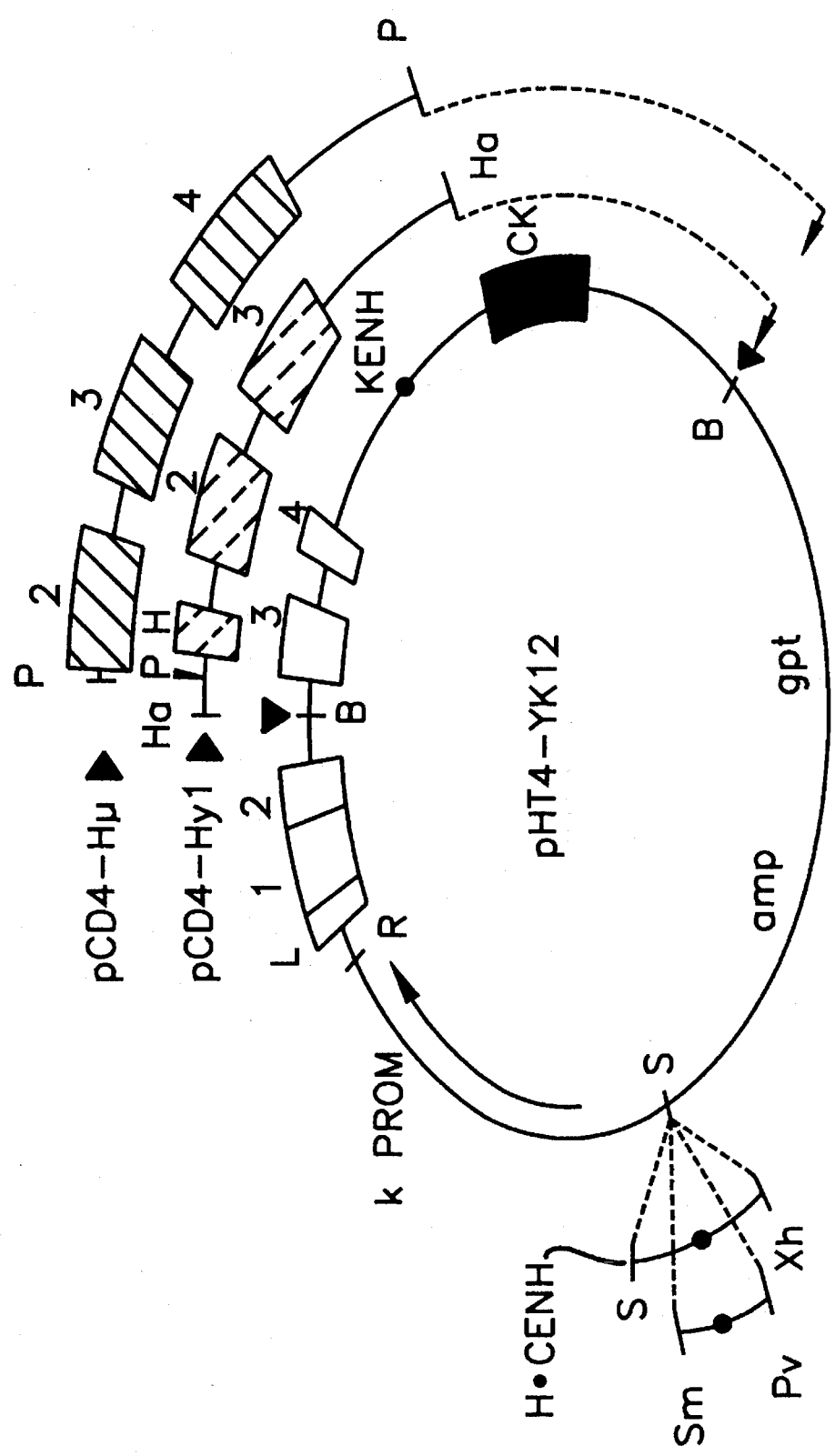
FIG. 2 shows plasmids pHT4-YK12 (see FIG. 1), pCD4-

Supernatant of COS-1 cells transfected with plasmid pshIL5Rα prepared as described in Example 10 was tested for the presence of secreted shIL5Rα in a competition binding assay as follows: COS-1 cells transfected as described in Example 10 with a plasmid comprising a cDNA coding for mIL5Rα (for amino acid sequence see SEQ. ID No: 1), obtained from a clone as described in Example 5 and constructed as described in Example 7, were detached by treatment with phosphate buffered saline (PBS) containing 0.5 mM EDTA and 0.02% sodium azide for 30 minutes at 37° C., resuspended at $1.5 \times 10^5$ cells per 0.3 ml binding medium (DMEM+10% FCS+0.02% sodium azide) and incubated with 0.8 nM $^{125}$I-mIL5 at 4° C. for 1 hour in the absence (FIG. 2; "+cold", non-specific binding) or presence (FIG. 2; "+cold", non-specific binding) of 100-fold excess unlabeled mIL5. Supernatant of COS-1 cells (80% of binding medium) transfected with pshIL5Rα was tested for its capacity to inhibit the binding of $^{125}$I-mIL5. Binding was also carried out in the presence of 80% supernatant of untransfected COS-1 cells. To separate cell membrane bound $^{125}$I-mIL5 from free radioactivity COS-1 cells were sedimented through a phthalate oil cushion and individual pellets were counted in a gamma counter as described, for example, see Plaetinck et al., J. Exp. Med. 172, 683–691 (1990).

EXAMPLE 12

Construction of a chimeric human IL5Rα-IgG1 molecule

As a first step, a polymerase chain reaction (PCR) was performed using plasmid pshIL5Rα as a template and using the following primers:

5'-CATAGACACGACAGACACGG [SEQ ID NO: 19], located in the 5' untranslated region of the hIL5Rα gene (position 104→123) and 5'-TACTGCAGATCCGCCTCTTGAGAACCCCACAT [SEQ ID NO: 20], a primer which matches the last 17 residues of the coding region of the hIL5Rα soluble form, with the addition of 15 residues coding for a Gly-Gly-Ser-Ala "linker" region, and a Pst1 recognition site. The PCR was performed using Vent Polymerase, under conditions as described by the manufacturer (New England BioLabs Inc., Beverly, Mass., USA).

After phenol extraction and ethanol precipitation, the PCR product was resuspended in an appropriate buffer, and was kinased by T4 kinase and blunted by Klenow Polymerase by methods described.

To the blunt ended PCR fragment, Bst X1 recognition sites were added, by ligation of 2 synthetic non-palindromic oligonucleotides with the sequence 5'-CTTTAGAGCACA [SEQ ID NO: 17] and

3'-GAAATCTC [SEQ ID NO: 18].

The resulting fragment was then ligated into Bst X1-opened pCDM8 vector.

The resulting plasmid containing the fragment in a sense orientation relative to the CMV promotor in pCDM8 was opened by Not1 cleavage, followed by a partial Pst1 restriction digestion. A Pst1-Eag1 restriction fragment was purified from the pBRHIG1 plasmid vector (Ellison et al.), and ligated into the plasmid vector described above.

The Eag1 and Not1 restriction enzymes generate the same sticky ends, and that fusion of both causes the loss of the Not1 recognition site, but not of the Eag1 recognition site. Hence, to favor the desired recombinant construct, a Not1 counterselection was performed.

EXAMPLE 13

Construction of a chimeric human IL5Rα-IgG3 molecule

The same protocol as description in Example 12 was used with the following exceptions:

The PCR 5' linker was:

```
                        Met
5'-AAGCTTGGATCCATGATCATCGTGGCGCAT    [SEQ ID NO: 21]
   Hind3   BamH1
``` which creates two extra restriction sites as indicated 5' to the nucleotides which match with the first 6 amino acids of hIL5Rα.

As PCR 3' linker the following nucleotide was used:

5'-GAGCTCACCGGATCCGCCTCTTGAGAACCCCACAT. [SEQ ID NO: 22]

In addition a partial Sac1 digest was used instead of a Pst1 digest and pATHIG3(2) (Huck et al. s.a.) was used as a source of the immunoglobulin gene part.

EXAMPLE 14

Construction of Plasmids

Plasmid constructions can be carried out using standard methodology as described by Maniatis, et al., "Molecular Cloning: A Laboratory Manual," Cold Spring Harbor Laboratory, New York (1982).

The starting plasmid for all constructions is designated pHT4-Y1 and can be prepared as previously described by Traunecker, Luke and Karjalainen in Nature, 331:84–86 (1988). This vector, carrying as selection markers the ampicillin resistance gene and the gpt gene (Mulligan and Berg, Science, 209:1422 (1980)), encodes in addition a hybrid protein composed of the whole extracellular portion of the human CD4 receptor fused to the mouse immunoglobulin kappa light-chain constant region.

Vector pHT4-Y1 was modified by replacing the mouse Ig heavy chain promoter by the more efficient mouse Ig kappa promoter derived from the vector pKm 1 (Traunecker et al., Eur. J. Immunol., 16:851–854 (1986)). The kappa promoter was first subcloned as a BglII/SalI fragment into the vector pUC18 digested with BamHI and SalI, recovered as a 2.2 kb HindIII (3' recessive ends filled with the help of the Klenow fragment of E. coli DNA polymerase, called hereafter: blunt)/EcoRI fragment and subsequently inserted into XbaI (blunt)/EcoRI digested pHT4-Y1 to generate plasmid pHT4-YK12 (see FIG. 1).

This plasmid was then digested with BamHI, to remove the exons 3 and 4 of the CD4 gene and the exon encoding the mouse Ig kappa light chain constant region, the 3' recessive ends were filled with Klenow polymerase and dephosphorylated with calf intestine alkaline phosphatase to facilitate the insertion of the following gene fragments (blunt ended before ligation):

a 3.5 kb SstI/XbaI DNA fragment containing the constant region exons C2, C3 and C4 of the mouse Ig μ heavy chain gene [Arnheim, N., et al., Cell, 22:179–185 (1980)]resulting in the preliminary plasmid pCD4-Mμ*.

a 3.0 kg StuI DNA fragment containing the Hinge and the C2 and C3 constant region exons of the mouse Igγ2 a heavy chain gene [Roeder, W., et al., PNAS, 78:474–479 (1981)] resulting in the preliminary plasmid pCD4-Mγ2a*.

a HaeII DNA fragment (made blunt with T4 DNA polymerase) containing the Hinge and the C2 and C3 constant region exons of the human Igγ1 heavy chain gene [Ellison, J. W., et al., Nucleic Acids Res., 10:4071–4079 (1982)] resulting in the preliminary plasmid pCD4-Hγ1*.

a DNA fragment containing the constant region exons C2, C3 and C4 of the human Ig μ heavy chain gene [Rabbits, T. H., et al., Nucleic Acids Res.,9:4509–4524 (1981)]. This DNA fragment was constructed as follows: first, the HaeII fragment of the human Ig γ1 heavy chain gene was made blunt ended as described and inserted into a blunt ended SalI site of pUC19 in an orientation positioning the Hinge exon towards the BamHI site. This intermediate construct was then digested with PstI to remove the 3 γ1 exons except for the splice acceptor site of the Hinge exon flanking the PstI site in the gene (the second PstI site is in the pUC19 polylinker), followed by the insertion of the PstI fragment of the human μ gene containing exons C2, C3 and C4 (Rabbits, et al., see above). This final gene construct was then recovered by BamHI and HindIII digestion (both sites in the pUC19 polylinker), followed by Klenow treatment and insertion into vector pHT4 YK12 as described above resulting in the preliminary plasmid pCD4-Hμ*.

The preliminary plasmids (pCD4-Mμ*, pCD4-Mγ2a*, pCD4-Hγ1*) were completed by inserting a XhoI SalI fragment which contains the murine μ heavy chain gene enhancer into the unique SalI site 5' to the promoter (see FIGS. 1 and 2) and the preliminary plasmid pCD4-Hμ was completed by inserting the murine μ "core" enhancer as a SmaI-PvuII fragment into the blunt-ended SalI site 5' to the promoter (FIG. 2), resulting in the final plasmids pCD4-Mμ, pCD4-Mγ2a, pCD4-Hγ1 and pCD4-Hμ. Originally the enhancer fragment XbaI EcoRI described by Gillies, et al. (Cell, 33:717–728, (1983)) was inserted, via an EcoRI-linker on XbaI, into the EcoRI site of the Bluescript vector (Stratagene, La Jolla, U.S.A.) in an orientation positioning the XbaI (EcoRI) site next to the EcoRV site. Into the unique SstI site of the vector an adaptor was inserted which contained a XhoI site. Finally, the enhancer fragment was recovered with XhoI-SalI for constructs pCD4-Mμ, pCD4-Mγ2a and pCD4-Hγ1or with SmaI-PvuII for construct pCD4-Hμ.

For the construction of pCD4-Hγ3 plasmid pHT4-YK12 (see FIG. 1) was digested with BamHI to remover the exons 3 and 4 of the CD4 gene and the exon encoding the mouse Ig kappa light chain constant region, and dephosphorylated with calf intestine alkaline phosphatase to facilitate the insertion of a 6.0 kb Bgl II DNA fragment containing the hinge and the C2 and C3 constant region exons of the human Igγ3 heavy chain gene [Huch, S., et al., Nucleic Acids Res., 14:1779–1789 (1986)] resulting in the preliminary plasmid pCD4-Hγ3*. The preliminary plasmid pCD4-Hγ3* was completed by inserting the murine μ "cae" enhancer as described above for plasmid pCD4-Hμ.

---

What is claimed is:

1. An isolated DNA molecule comprising:

(a) a first DNA subsequence encoding the α-chain of the interleukin-5 receptor capable of binding human interleukin-5; and (b) a second DNA subsequence comprising a DNA sequence encoding a constant domain of a heavy chain of a human immunoglobulin;

the first DNA subsequence and the second DNA subsequence being linked 5'-3'.

2. The DNA molecule according to claim 1, wherein the second DNA subsequence encodes all domains, except the first domain, of the constant region of a heavy chain of a human immunoglobulin selected from the group consisting of IgG, IgA, IgM and IgE.

3. The DNA molecule according to claim 2, wherein the human immunoglobulin is selected from the group consisting of IgM and IgG.

4. The DNA molecule according to claim 3, wherein the human immunoglobulin is IgG of the IgG1 or IgG3 type.

5. A vector comprising a DNA sequence, the DNA sequence comprising:

(a) a first DNA subsequence encoding the α-chain of the interleukin-5 receptor capable of binding human interleukin-5; and (b) a second DNA subsequence comprising a DNA sequence encoding a constant domain of a heavy chain of a human immunoglobulin;

the first DNA subsequence and the second DNA subsequence being linked 5'-3'.

6. The vector according to claim 5, wherein the second DNA subsequence encodes all domains, except the first domain, of the constant region of a heavy chain of a human immunoglobulin selected from the group consisting of IgG, IgA, IgM and IgE.

7. The vector according to claim 6, wherein the human immunoglobulin is selected from the group consisting of IgM and IgG.

8. The vector according to claim 7, wherein the human immunoglobulin is IgG of the IgG1 or IgG3 type.

9. A prokaryotic or eukaryotic host cell transformed with a vector, the vector comprising a DNA sequence, the DNA sequence comprising:

(a) a first DNA subsequence encoding the α-chain of the interleukin-5 receptor capable of binding human interleukin-5; and (b) a second DNA subsequence comprising a DNA sequence encoding a constant domain of a heavy chain of a human immunoglobulin;

the first DNA subsequence and the second DNA subsequence being linked 5'-3'.

10. The host cell according to claim 9, wherein the second DNA subsequence encodes all domains, except the first domain, of the constant region of a heavy chain of a human immunoglobulin selected from the group consisting of IgG, IgA, IgM and IgE.

11. The host cell according to claim 10, wherein the human immunoglobulin is selected from the group consisting of IgM and IgG.

12. The host cell according to claim 11, wherein the human immunoglobulin is IgG of the IgG1 or IgG3 type.

13. An isolated DNA molecule comprising:
   (a) a first DNA subsequence encoding a fragment of the α-chain of the interleukin-5 receptor capable of binding human interleukin-5, selected from the group consisting of:
      (i) a DNA sequence comprising the DNA sequence of SEQ ID NO: 1 or its complementary strand, and
      (ii) a DNA sequence which, because of the degeneracy of the genetic code, for a polypeptide having exactly the same amino acid sequence as the fragment of the α-chain of the human interleukin-5 receptor defined under (i); and
   (b) a second DNA subsequence comprising a DNA sequence encoding a constant domain of a heavy chain of a human immunoglobulin;
the first DNA subsequence and the second DNA subsequence being linked 5'-3'.

14. The DNA molecule according to claim 13, wherein the first DNA subsequence is a DNA sequence comprising the DNA sequence of SEQ ID NO: 1 or its complementary strand.

15. A vector comprising a DNA molecule, the DNA molecule comprising:
   (a) a first DNA subsequence encoding a fragment of the α-chain of the interleukin-5 receptor capable of binding human interleukin-5, selected from the group consisting of:
      (i) a DNA sequence comprising the DNA sequence of SEQ ID NO: 1 or its complementary strand, and
      (ii) a DNA sequence which, because of the degeneracy of the genetic code, codes for a polypeptide having exactly the same amino acid sequence as the fragment of the α-chain of the human interleukin-5 receptor defined under (i); and
   (b) a second DNA subsequence comprising a DNA sequence encoding a constant domain of a heavy chain of a human immunoglobulin;
the first DNA subsequence and the second DNA subsequence being linked 5'-3'.

16. The vector according to claim 15, wherein the first DNA subsequence is a DNA sequence comprising the DNA sequence of SEQ ID NO: 1 or its complementary strand.

17. A prokaryotic or eukaryotic host cell transformed with a vector, the vector comprising a DNA molecule, the DNA molecule comprising:
   (a) a first DNA subsequence encoding a fragment of the α-chain of the interleukin-5, receptor capable of binding human interleukin-5, selected from the group consisting of:
      (i) a DNA sequence comprising the DNA sequence of SEQ ID NO: 1 or its complementary strand, and
      (ii) a DNA sequence which, because of the degeneracy of the genetic code, codes for a polypeptide having exactly the same amino acid sequence as the fragment of the α-chain of the human interleukin-5 receptor defined under (i); and
   (b) a second DNA subsequence comprising a DNA sequence encoding a constant domain of a heavy chain of a human immunoglobulin;
the first DNA subsequence and the second DNA subsequence being linked 5'-3'.

18. The host cell according to claim 17, wherein the first DNA subsequence is a DNA sequence comprising the DNA sequence of SEQ ID NO: 1 or its complementary strand.

* * * * *

UNITED STATES PATENT AND TRADEMARK OFFICE
CERTIFICATE OF CORRECTION

PATENT NO. : 5,455,337
DATED      : October 3, 1995
INVENTOR(S) : ReneDevos, Walter Fiers, Jose van der Heyden,
              Geert Plaetinck, Jan Tavernier It is certified that error appears in the above-indentified patent and that said Letters Patent is hereby corrected as shown below:

In claim 13, column 33, line 14, after "," and before "for", insert -- codes --.

Signed and Sealed this

Twelfth Day of March, 1996

Attest:

BRUCE LEHMAN

Attesting Officer       Commissioner of Patents and Trademarks